United States Patent [19]

Fogarty

[11] 4,315,512

[45] Feb. 16, 1982

[54] PISTON EXTENSION BALLOON DILATATION CATHETER APPARATUS AND METHOD

[76] Inventor: Thomas J. Fogarty, 770 Welch Rd., Palo Alto, Calif. 94304

[21] Appl. No.: 114,982

[22] Filed: Jan. 24, 1980

[51] Int. Cl.³ .......................................... A61M 29/02
[52] U.S. Cl. ................................ 128/344; 128/349 B
[58] Field of Search ........ 128/349 B, 349 BV, 349 R, 128/344, 341, 348, 325, 241, 242, 243, 246, DIG. 16, DIG. 9

[56] References Cited

U.S. PATENT DOCUMENTS

| | | | |
|---|---|---|---|
| 419,926 | 1/1890 | Chapman | 128/349 R |
| 2,460,473 | 2/1949 | Smith | 128/349 R |
| 3,344,791 | 10/1967 | Foderick | 128/349 R |
| 3,433,215 | 3/1969 | Silverman | 128/2 |
| 3,833,003 | 9/1974 | Taricco | 128/347 |
| 3,834,394 | 9/1974 | Hunter et al. | 128/325 |
| 3,896,815 | 7/1975 | Fettel et al. | 128/348 |
| 3,970,090 | 7/1976 | Loiacono | 128/349 R |
| 3,978,863 | 9/1976 | Fettel et al. | 128/348 |
| 3,996,938 | 12/1976 | Clark | 128/348 |

FOREIGN PATENT DOCUMENTS 2847633  10/1979  Fed. Rep. of Germany ... 128/349 B

Primary Examiner—Gene Mancene
Assistant Examiner—Mickey Yu
Attorney, Agent, or Firm—Naylor, Neal & Uilkema

[57] ABSTRACT

An elastomeric balloon is secured to one end of a catheter and stretched in order to reduce the balloon cross-section and facilitate its placement within an occluded section of a blood vessel. Stretching of the balloon is achieved by attaching the mouth of the balloon to the distal end of the catheter and extending the body of the balloon with a piston carried by the catheter for extension relative thereto. Once in place, the balloon is expanded through the injection of a volume of fluid into the catheter, thereby pressing the occlusion against the wall of the blood vessel to increase the patency of the vessel.

16 Claims, 8 Drawing Figures

PISTON EXTENSION BALLOON DILATATION CATHETER APPARATUS AND METHOD

BACKGROUND OF THE INVENTION

The present invention relates to a method and apparatus for use in dilating occluded blood vessels. The invention is particularly concerned with such a method and apparatus wherein dilatation is achieved through means of a balloon element which is initially stretched to reduce its cross-section and facilitate its placement within the vessel and, once in place, inflated to compress occlusions within the vessel. The invention is intended for use in treating either arterial or venous occlusions.

RELATED APPLICATION

The present application is related to copending Application Ser. No. 60,408, now U.S. Pat. No. 4,271,839, filed July 25, 1979, by Thomas J. Fogarty and Albert K. Chin. That application is also concerned with a method and apparatus for placing an inflatable balloon within an occluded section of a blood vessel for purposes of increasing the patency of the vessel. It differs materially from the present application in that the inflatable balloon disclosed therein is initially inverted within the distal end of a flexible catheter and ultimately everted from the catheter through the employment of fluid pressure. In the invention of the present application, the balloon initially assumes a condition mechanically extended from the catheter to reduce the cross-section of the balloon and facilitate its placement.

SUMMARY OF THE INVENTION

The present invention relies upon the concept that the elongation of a balloon by mechanical means will reduce the cross-section of the balloon and, thus, facilitate its placement within confined areas. As embodied in the apparatus and method of the invention, the balloon is preferably elastomeric and attached to the open distal end of a flexible catheter. Balloon elongation is accomplished through the use of a piston which is free to slide within the lumen of the catheter. The distal end of the balloon is attached to the tip of the piston and the mouth (proximal end) of the balloon is attached to the catheter. Extension of the piston is achieved through means of a stylet which extends slidably through the catheter. Stops are provided to prevent separation of the piston from the catheter and limit extension of the piston. In the preferred embodiment, the piston is flexible in order to minimize the possibility of injury to the vessel being treated, or the dislodgement of plaque material.

In one application of the invention, the balloon is reduced in cross-section for passage through a precutaneous needle. The purpose of the piston extension in this case is to allow a balloon which is of a larger diameter than the needle to pass through the needle and into a large diameter blood vessel. Once within the vessel, the piston may be relaxed to allow the balloon to contract for passage through the artery. Alternatively, where the passage through the vessel is very restricted, the piston may be held in the extended condition so as to maintain the balloon in a condition of reduced cross-section.

A principal object of the present invention is to provide a balloon catheter wherein the balloon cross-section can be decreased by mechanically extending the length of the balloon.

Another and related object of the invention is to provide a balloon catheter wherein the balloon is fabricated of relatively thick-walled elastomeric material which may be reduced in thickness through stretching of the balloon in order to decrease the lateral cross-section of the balloon.

Still another object of the invention is to provide a balloon catheter wherein the length of the balloon element employed in the catheter may be easily varied from a design and mechanical standpoint.

A further object of the invention is to provide a balloon catheter wherein both the proximal and distal ends of the balloon are secured against separation from the catheter in the event the balloon ruptures.

Another object of the invention is to provide a balloon catheter wherein the inflated length of the balloon may be selectively varied.

Yet another object of the invention is to provide a balloon catheter wherein the balloon element is not dependent upon the application of fluid pressure to facilitate its initial placement within the vessel being treated.

The foregoing and other objects will become more apparent when viewed within light of the accompanying drawings and the following description.

DESCRIPTION OF THE ILLUSTRATED EMBODIMENTS

Figure 1:
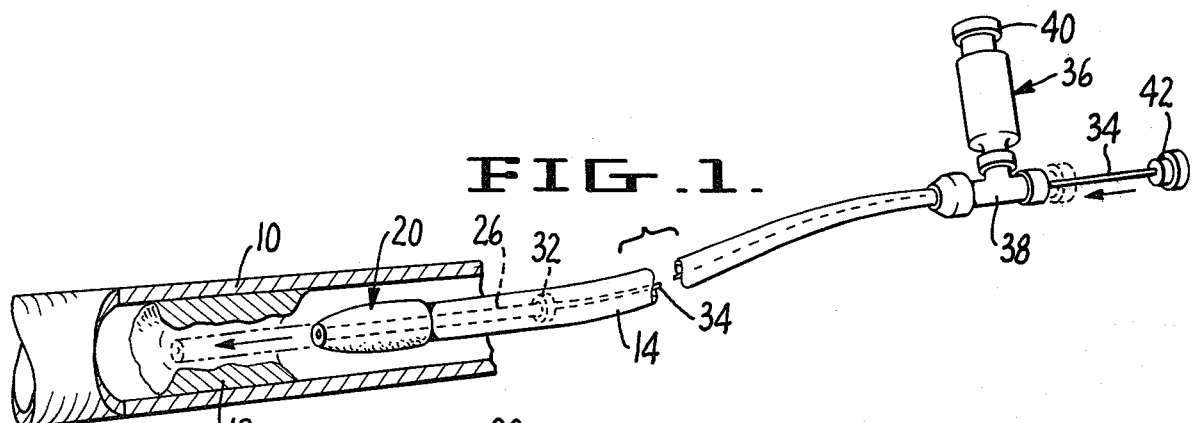
FIG. 1 is a perspective view illustrating an occluded vessel in the process of having the catheter of the present invention placed therein.
Figure 2:
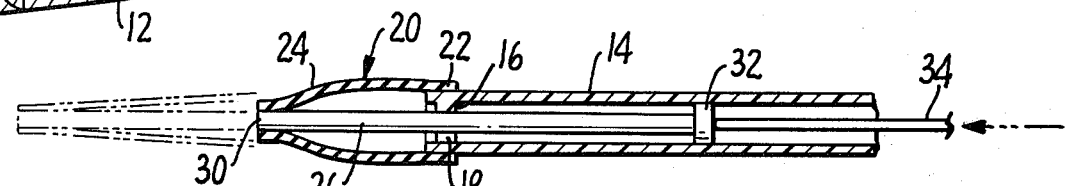
FIG. 2 is an elevational cross-sectional view illustrating the catheter of the present invention, with solid lines showing the balloon element in the nonextended condition and phantom lines showing the ballon element stretched to the extended reduced cross-section condition.

FIG. 1 illustrates a blood vessel 10 partially occluded by an occlusion 12. As shown, the vessel takes the form of an artery and the occlusion is what is commonly known as an arteriosclerotic plaque or atheroma. This is the type of adhering occlusion with which the inventive apparatus and method is expected to find primary application. It should be understood, however, that the invention is applicable in treating other types of occluded vessels where dilatation is desired. For example, the invention may be used in treating occlusions resulting from fibromuscular-displasia in veins.

Figure 3:
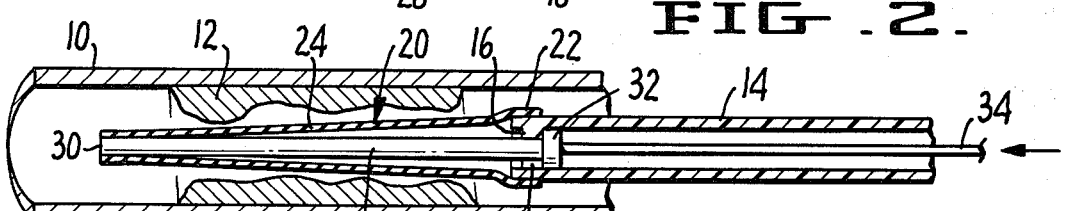
FIG. 3 is a cross-sectional elevational view illustrating the catheter with the balloon element in the extended stretched condition, as it would appear when first positioned within an occluded section of a vessel to be treated.
Figure 4:
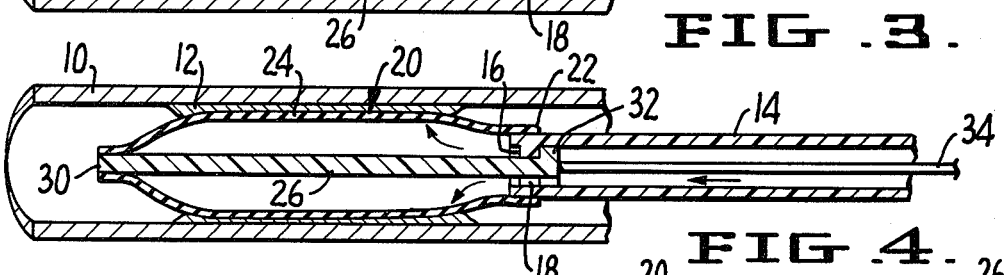
FIG. 4 is a cross-sectional elevational view, similar to FIG. 3, illustrating the balloon element after it has been inflated to dilate the occlusion being treated.

The principal elements of the apparatus shown in FIGS. 1 to 4 comprise: a flexible generally inelastic catheter 14 fabricated of an inert polymer material, such as Dacron; a stop collar 16 formed integrally with the catheter 14 within the distal end thereof, said collar having a passage 18 extending therethrough; a balloon 20 fabricated of an elastomeric material, such as latex, said balloon having an open mouth 22 sealingly secured in fluid communication with the distal end of the catheter and a body portion 24 extending longitudinally from the catheter; a piston 26 slidably received within the catheter 14, said piston having an elongated body extending slidably through the collar 16, a distal end 30 sealingly secured to the distal end of the balloon 20, and a stop flange 32 disposed for abutting engagement with the collar 16 upon extension of the piston (as shown in FIGS. 3 and 4); and, a flexible stylet 34 extending through the catheter for engagement with the flange 32 to selectively extend and retract the piston.

A syringe 36 is connected to the proximal end of the catheter 14 through a T-shaped coupling 38. The syringe and catheter are filled with an incompressible fluid and a plunger 40 forming part of the syringe provides means whereby this fluid may be selectively charged into or released from the balloon 20 through the catheter 14. The stylet 34 extends slidably through a packing (not illustrated) therefor in the coupling 38. The packing sealingly engages the stylet to prevent the escape of fluid therearound. A knob 42 is secured to the proximal end of the stylet 34 externally of the coupling 38 to provide means whereby the stylet may be moved longitudinally relative to the catheter to impart movement to the piston 26.

The catheter 14 may vary in length, depending upon the application in which it is intended to be used. It commonly measures up to 30 inches in length. The cross-sectional dimensions of the catheter may vary, depending upon the application, and are generally chosen so that the outside diameter of the catheter is equal to about one-half of the inner diameter of the nonoccluded lumen of the vessel being treated.

The material and dimensions of the balloon 20 are chosen so that the balloon may be stretched lengthwise by the piston 26 to reduce the cross-sectional dimensions of the balloon sufficiently to permit its passage through the occlusion being treated, without danger of dislodging material from the occlusion. In the preferred embodiment, the balloon is an elastomeric material, such as latex, and stretching of the balloon responsive to extension of the piston functions to reduce the external diameter of the body portion 24 to a dimension equal to or less than the outside diameter of the catheter 14. The material and dimensions of the balloon are also chosen so that the balloon may be extended through a substantial length of the occlusion being treated and have sufficient strength to minimize the possibility of bursting upon inflation.

In the embodiment illustrated in FIGS. 1 to 4, the piston 26 is of solid construction and fabricated of a strong flexible material, such as nylon. A passage 44 (see FIG. 4) extends through the stop flange 32 to permit fluid to be displaced through the flange by the syringe 40.

Figure 5:
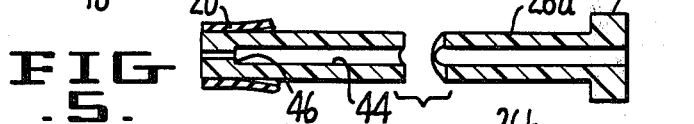
FIG. 5 if a cross-sectional elevational view, with parts thereof broken away, showing a piston of a hollow body construction which may be employed in the catheter of the present invention.
Figure 6:
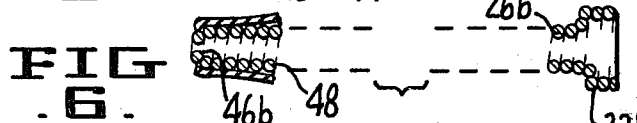
FIG. 6 is a cross-sectional elevational view, with parts thereof broken away, showing a piston of a helical coil construction which may be used in the catheter of the present invention.

FIGS. 5 and 6 illustrate alternative constructions for the piston employed in the apparatus of the present invention.

The piston shown in FIG. 5, designated 26a, is fabricated of a polymer material, such as nylon, and has a passage 44 extending longitudinally therethrough for receipt of the stylet 34. The distal end of the passage 44 is provided with a shoulder 46 for abutting engagement with the end of the stylet. As compared with the solid piston shown in FIGS. 2 to 4, the piston 44 may be of somewhat lighter construction and stiffened through extension of the stylet through the passage 44. The balloon 20 is sealingly secured to the distal end of the piston 26a and a stop flange 32a is formed on the proximal end of the piston 26a for abutment with the stop collar 16.

The piston shown in FIG. 6 is designated by the numeral 26b. This piston comprises a resilient coil spring 48 having the balloon 20 sealingly secured to the distal end thereof and a stop flange 32b integrally formed with the proximal end thereof for abutment with the stop collar 16. The body of the spring 48 may be covered with an impermeable coating so as to be impervious to the passage of fluid therethrough. If the spring is not provided with such a coating, the distal end of the balloon must be sealed in order that the balloon may be inflated. The piston 26b is highly flexible and designed to have the stylet extended therethrough. The coils at the distal end of the spring 48 are of reduced diameter to provide a shoulder 46b against which the stylet may abut.

As shown in FIG. 1, the catheter is inserted into the vessel being treated and directed to the situs of the occlusion with the balloon in a relaxed condition. Once adjacent the occlusion, the piston 26 is extended through the application of axial force to the stylet 34, as shown by the arrow lines in FIGS. 1, 2 and 3. Such extension functions to reduce the lateral cross-section of the balloon and direct it through the occlusion, as shown in FIG. 3. After being extended through the occlusion, as shown in FIG. 4, the balloon is inflated by applying internal pressure thereto through the syringe 36. Inflation of the balloon, in turn, functions to compress the occlusion and increase the patency of the vessel being treated.

As shown in FIG. 4, the piston 26 is maintained in the extended condition during inflation of the balloon. This has the advantage that the balloon assumes an elongated configuration ideally suited to compress an elongate section of plaque.

Once treatment of an occluded section of the vessel is complete, the balloon may be deflated and the catheter may be moved to successive occluded sections of the vessel in order that the balloon may be reinflated for treatment of these sections. Depending upon the nature of the path between successive sections, the balloon may be relaxed to the condition shown in FIG. 2 as it is moved and, upon reaching a successive occluded section, re-extended, as shown in FIG. 3, and then inflated, as shown in FIG. 4.

Figure 7:
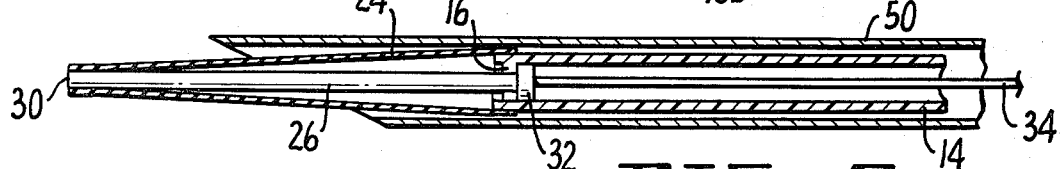
FIG. 7 is a cross-sectional elevational view showing the catheter of the present invention received within a percutaneous needle, with the balloon element of the catheter extended to a condition of reduced cross-section for passage through the needle.

FIG. 7 illustrates the manner in which the present invention may be used in association with a percutaneous needle. The needle is designated by the numeral 50 and the catheter is illustrated as extending therethrough. As shown, the piston 26 is extended to reduce the diameter of the balloon and thus facilitate its extension through the needle.

Figure 8:
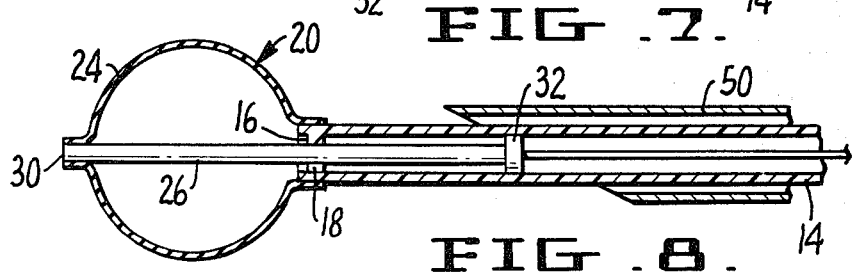
FIG. 8 is a cross-sectional elevational view of the invention showing the catheter extending through a percutaneous needle, with the balloon element in an inflated condition and the piston in a relaxed condition.

In FIG. 8, the distal end of the catheter is external of the tip of the needle and the balloon has been inflated, with the piston in a relaxed condition. Such inflation of the balloon results in a generally spherical balloon configuration, as contrasted to the elongated configuration shown in FIG. 4. Thus, it should be appreciated that the inflated length of the balloon may be selectively varied by varying the degree to which the piston is extended during inflation.

CONCLUSION

Although preferred embodiments of the invention have been illustrated and described, it should be understood that the invention is not intended to be limited to the specifics of the embodiments, but rather is defined by the accompanying claims.

What is claimed is:

1. Apparatus for dilating a partially occluded section of a blood vessel, said apparatus comprising: an elongated flexible catheter adapted for passage through the vessel, said catheter having an open distal end; an elastomeric balloon having a mouth sealingly secured in fluid communication with the open distal end of the catheter; a piston connected to the balloon and slidably received within the catheter for movement relative thereto between an extended condition wherein the piston stretches the balloon lengthwise and a retracted position wherein the piston releases the balloon from such stretching; means to selectively move the piston between the retracted and extended conditions; said balloon having an outer diameter in its uninflated and extended condition which is less than the outer diameter of said catheter; and means to impart internal fluid pressure to the catheter to selectively inflate the balloon.

2. Apparatus according to claim 1 further comprising stop means to prevent separation of the piston from the catheter and limit extension of the piston relative to the open distal end of the catheter.

3. Apparatus according to claim 1 wherein the means to selectively move the piston comprises a stylet extending through the catheter for abutting engagement with the piston.

4. Apparatus for dilating a partially occluded section of a vessel, said apparatus comprising: an elongated flexible catheter adapted for passage through the vessel, said catheter having an open distal end; an inflatable balloon having a mouth sealingly secured in fluid communication with the open distal end of the catheter; a piston connected to the balloon and slidably associated with the catheter for movement relative thereto between a condition extending the balloon lengthwise of the catheter and a condition relaxing the balloon from such extension; said balloon having an outer diameter in its uninflated and extended condition which is less than the outer diameter of said catheter; and stop means to prevent separation of the piston from the catheter and limit movement of the piston in the direction extending the balloon lengthwise of the catheter.

5. Apparatus according to claim 4 further comprising a stylet extending through the catheter for abutting engagement with the piston to selectively move the piston between the conditions extending and relaxing the balloon.

6. Apparatus for dilating a partially occluded section of a blood vessel, said apparatus comprising: an elongated flexible catheter adapted for passage through the vessel, said catheter having an open distal end; an elastomeric balloon having a mouth sealingly secured in fluid communication with the open distal end of the catheter; a piston connected to the balloon and slidably received within the catheter for movement relative thereto between an extended condition wherein the piston stretches the balloon lengthwise and a retracted position wherein the piston releases the balloon from such stretching; means to selectively move the piston between the retracted and extended conditions; and means to impart internal fluid pressure to the catheter to selectively inflate the balloon, said means to selectively move the piston comprising a stylet extending through the catheter for abutting engagement with the piston, said piston comprising a flexible tubular body having a passage extending therein for slidable receipt of the stylet and a stop at the distal end of the passage for abutting engagement with the stylet.

7. Apparatus according to claim 6 wherein the body comprises a flexible coil spring having convolutions defining the passage.

8. Apparatus according to claim 6 wherein the body is fabricated of a flexible polymer material.

9. Apparatus for dilating a partially occluded section of a vessel, said apparatus comprising: an elongated flexible catheter adapted for passage through the vessel, said catheter having an open distal end; an inflatable balloon having a mouth sealingly secured in fluid communication with the open distal end of the catheter; a piston connected to the balloon and slidably associated with the catheter for movement relative thereto between a condition extending the balloon lengthwise of the catheter and a condition relaxing the balloon from such extension; stop means to prevent separation of the piston from the catheter and limit movement of the piston in the direction extending the balloon lengthwise of the catheter; and a stylet extending through the catheter for abutting engagement with the piston to selectively move the piston between the conditions extending and relaxing the balloon; said piston comprising a flexible tubular body having a passage therein for slidable receipt of the stylet and a stop at the distal end of the passage for abutting engagement with the stylet.

10. Apparatus according to claim 9 wherein the body comprises a flexible coil spring having convolutions defining the passage.

11. Apparatus according to claim 9 wherein the body is fabricated of a flexible polymer material.

12. A method for inserting an inflatable balloon into a partially occluded section of a blood vessel, said method comprising: securing the mouth of the balloon in sealed fluid communication with the distal end of a flexible catheter proportioned for passage through the vessel; extending a piston from the distal end of the catheter and into engagement with the balloon to extend the balloon lengthwise and reduce its lateral cross-sectional dimension in its uninflated condition to a value less than the lateral cross-sectional dimension of said catheter; and directing the catheter into the vessel with the balloon so extended.

13. A method according to claim 12 further comprising passing the balloon into the occluded section of the vessel while maintaining the balloon in the lengthwise extended condition.

14. A method according to claim 13 further comprising: relaxing the extension of the piston after placement of the balloon within the occluded section of the vessel to permit the balloon to contract lengthwise; and, inflating the balloon to laterally compress the occluded section.

15. A method according to claim 14 further comprising: securing the piston between the catheter and balloon to limit lengthwise extension of the balloon relative to the catheter and prevent separation of the balloon from the catheter.

16. A method according to claim 13 further comprising inflating the balloon within the occluded section of the vessel while maintaining the balloon in the lengthwise extended condition through extension of the piston.

* * * * *